United States Patent

Klieger et al.

[11] 4,264,572
[45] Apr. 28, 1981

[54] X-RAY CONTRAST MEDIA

[75] Inventors: Erich Klieger; Wolfgang Mützel, both of Berlin, Fed. Rep. of Germany

[73] Assignee: Schering Aktiengesellschaft, Berlin and Bergkamen, Fed. Rep. of Germany

[21] Appl. No.: 99,172

[22] Filed: Nov. 30, 1979

[30] Foreign Application Priority Data

Nov. 30, 1978 [DE] Fed. Rep. of Germany ....... 2852094

[51] Int. Cl.³ ..................... A61K 49/04; C07C 101/48
[52] U.S. Cl. ......................................... 424/5; 560/37; 560/42; 562/442; 562/451; 260/326.41; 546/221; 546/226
[58] Field of Search ..................... 424/5; 562/455, 442, 562/451, 456; 260/326.41; 546/221, 226; 560/45, 42, 37, 47

[56] References Cited

U.S. PATENT DOCUMENTS

| | | | |
|---|---|---|---|
| 3,939,204 | 2/1976 | Buttermann | 424/5 |
| 3,953,501 | 4/1976 | Klieger et al. | 424/5 |
| 4,005,188 | 1/1977 | Tilly et al. | 424/5 |
| 4,065,553 | 12/1977 | Tilly et al. | 562/451 |
| 4,094,966 | 6/1978 | Tilly et al. | 424/5 |
| 4,132,731 | 1/1979 | Klieger et al. | 424/5 |

*Primary Examiner*—Natalie Trousof
*Assistant Examiner*—James H. Reamer
*Attorney, Agent, or Firm*—Millen & White

[57] ABSTRACT

Compounds of the formula

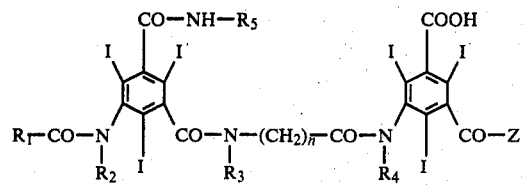

wherein
$R_1$ is $C_{1-4}$ alkyl, $C_{1-4}$ alkyl substituted by OH or $C_{1-2}$ alkoxy; $R_2$, $R_3$ and $R_4$ are independently each hydrogen or $C_{1-4}$ alkyl; Z is —A—$NHCH_3$ or when $R_1$ is hydroxy or alkoxy substituted alkyl and/or when $R_3$ is lower alkyl, Z can also be hydroxy-$C_{2-5}$-alkylamino;
$R_5$ is $C_{1-4}$ alkyl or $C_{1-4}$ alkyl substituted by OH; n is 1, 2 or 3; and A is:

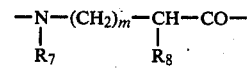

wherein
$R_7$ is H or $C_{1-4}$ alkyl; $R_8$ is H, $C_{1-4}$ alkyl or $C_{1-4}$ alkyl substituted by OH or $C_{1-2}$ alkoxy; or together $R_7$ and $R_8$ form a propylene or hydroxypropylene ring; and m is 0 or 1;
or an ester thereof with a $C_1$-$C_4$ alkanol or a physiologically acceptable salt thereof with a base, are valuable as X-ray contrast media.

13 Claims, No Drawings

X-RAY CONTRAST MEDIA

The present invention relates to new X-ray contrast agents.

SUMMARY OF THE INVENTION

It is an object of the present invention to provide derivatives of isophthalamic acid which have advantageous properties for use as contrast agents.

Upon further study of the specification and appended claims, further objects and advantages of this invention will become apparent to those skilled in the art.

These objects have been attained by this invention by providing new compounds of Formula I $$\text{R}_1-\text{CO}-\underset{\text{R}_2}{\text{N}} \left[ \text{Ar}_1 \right] \text{CO}-\underset{\text{R}_3}{\text{N}}-(\text{CH}_2)_n-\text{CO}-\underset{\text{R}_4}{\text{N}} \left[ \text{Ar}_2 \right] \text{CO}-\text{Z} \quad (I)$$

where Ar₁ bears CO—NH—R₅ and I substituents, and Ar₂ bears COOH and I substituents.

wherein
$R_1$ is $C_{1-4}$ alkyl, $C_{1-4}$ alkyl substituted by OH or $C_{1-2}$ alkoxy; $R_2$, $R_3$ and $R_4$ are independently each hydrogen or $C_{1-4}$ alkyl; Z is —A—NHCH$_3$ or when $R_1$ is hydroxy or alkoxy substituted alkyl and/or when $R_3$ is lower alkyl, Z can also be hydroxy-$C_{2-5}$-alkylamino;
$R_5$ is $C_{1-4}$ alkyl or $C_{1-4}$ alkyl substituted by OH; n is 1, 2 or 3; and A is $$-\underset{\text{R}_7}{\text{N}}-(\text{CH}_2)_m-\underset{\text{R}_8}{\text{CH}}-\text{CO}-$$

wherein
$R_7$ is H or $C_{1-4}$ alkyl; $R_8$ is H, $C_{1-4}$ alkyl or $C_{1-4}$ alkyl substituted by OH or $C_{1-2}$ alkoxy; or together $R_7$ and $R_8$ form a propylene or hydroxypropylene ring; and m is 0 or 1; or an ester thereof with a $C_1$-$C_4$ alkanol or a physiologically acceptable salt thereof with a base.

DETAILED DISCUSSION

The lower alkyl residue $R_1$, which where appropriate can be substituted singly or multiply, may contain from 1 to 4 carbon atoms, preferably 1 to 2 carbon atoms, in the alkyl residue. Suitable substituents include hydroxy, preferably 1-2 groups, or alkoxy of 1-2 carbon atoms, preferably one group. Preferred lower alkyl residues $R_1$ have 1-2 carbon atoms and may be substituted by hydroxy or alkoxy, such as, e.g., methyl, ethyl, methoxymethyl, hydroxymethyl and the like.

Suitable lower alkyl residues for $R_2$, $R_3$ and $R_4$ have 1-4 carbon atoms, preferably 1-2 carbon atoms, for instance methyl, ethyl, propyl, isopropyl and the like.

Suitable lower alkyl residues for $R_5$ have 1-4 carbon atoms and especially have 1-2 carbon atoms, for instance, methyl or ethyl. This alkyl residue may optionally be substituted by hydroxy, preferably 1-2 groups; n preferably has a value of 1.

When Z is straight-chain or branched hydroxy lower alkylamino, the alkyl residue may contain 2-5 carbon atoms, and, e.g., 1-3 hydroxy substituents. If Z is a straight chain group, the alkyl residue preferably contains 2-5 carbon atoms; if Z is branched, the alkyl residue preferably contains 3-5 carbon atoms. The hydroxy groups in Z may be present as primary or secondary hydroxy groups. Suitable Z residues include, e.g., 2-hydroxypropylamino, 3-hydroxypropylamino, 2-hydroxy-1, 1-dimethylethylamino, 3-hydroxy-1, 1-dimethylpropylamino and, preferably, 2-hydroxyethylamino.

Suitable bridging amino acid residues A include those derived from an amino carboxylic acid of arbitrary configuration. Included are those residues which are equivalents of, e.g., the preferred amino acid residue of the formula $$-\underset{\text{R}_7}{\text{N}}-(\text{CH}_2)_m-\underset{\text{R}_8}{\text{CH}}-\text{CO}-$$

wherein m is 0 or 1, $R_7$ is hydrogen or lower alkyl of 1-4 carbon atoms, preferably 1-2 carbon atoms, $R_8$ is hydrogen or lower alkyl of 1-4 carbon atoms which also may be straightchain or branched and which may be substituted by hydroxy, preferably 1-2 groups or lower alkoxy of 1-2 carbon toms, preferably 1-2 groups, and wherein $R_7$ and $R_8$ together may form a propylene or hydroxypropylene group. Examples of suitable aminocarboxylic acids include glycine, alanine, valine, serine, O-methylserine, proline, hydroxyproline, leucine, isoleucine, sarcosine, beta-alanine and the like. Especially preferred are α-amino-carboxylic acids in which $R_7$ is hydrogen or methyl and $R_8$ is hydrogen or lower alkyl of 1-2 carbon atoms which may be hydroxy- or methoxy-substituted.

To form salts, any of the conventional physiologically acceptable bases are suitable. These include, for instance, amines such as glucamine, ethanolamine, methylglucamine, etc.; basic aminoacids such as lysine, ornithine, arginine, etc.; or their amides or alkylesters; or bases yielding metal salts such as those of Na, K, Ca, Mg or mixtures of these.

The esterification of the free carboxy group may be conventionally carried out using physiologically acceptable alcohols. These include equivalents of the preferred lower alkanols of 1-4 carbon atoms, such as methanol, ethanol, propanol, butanol, etc.

The new compounds of this invention may be prepared be reacting an amine of Formula II $$\text{H}-\underset{\text{R}_3}{\text{N}}-(\text{CH}_2)_n-\text{CO}-\underset{\text{R}_4}{\text{N}} \left[ \text{Ar} \right] \text{COZ} \quad (II)$$

with COOH and I substituents on the ring.

wherein $R_3$, $R_4$, Z and n are as defined for Formula I above,
with a reactive functional derivative of Formula III $$\text{R}_6-\underset{\text{R}_2}{\text{N}} \left[ \text{Ar} \right] \text{CO}-X \quad (III)$$

with CO—NH—R₅ and I substituents on the ring.

wherein $R_2$ and $R_5$ are as defined above, —CO—X— is a reactive derivative form of the acid (III) and $R_6$ is hydrogen or —CO—$R_1$ wherein $R_1$ is as defined above;

and optionally acylating the aromatic amino group; and/or alkylating an amino group; and/or forming a physiologically acceptable salt or alkylester of the resultant product.

Suitable reactive acid derivatives include the following: anhydrides thereof with organic and inorganic acids such as with halogen hydracids, nitrogen hydracids or carboxylic acid half esters, or the reactive esters thereof such as their easily accessible alkylesters, arylesters or cyanomethylesters. The reactive acid residue X in Formula III accordingly can be an acid residue such as —Cl, —Br, —I, azido, another alkoxycarbonyloxy residue or the residue of a reactive ester group such as —O-alkyl, —O-aryl or —O—CH$_2$—C≡N. The preferred reactive acid residues are acid halides, preferably acid chlorides.

The amidation reaction preferably is carried out in a polar solvent at 0°–100° C., preferably 20°–80° C. Suitable solvents include water, dioxane, tetrahydrofuran, methylene chloride, trichloroethylene, dimethylformamide, dimethylacetamide, etc., and mixtures thereof. Advantageously, tertiary amines can be used to neutralize the hydrogen chloride generated in the reaction, for instance, triethylamine, tributylamine, or pyridine, or also alkali metal hydroxides or carbonates or alkaline earth hydroxides or carbonates such as KOH, NaOH, NaHCO$_3$, Na$_2$CO$_3$, Mg(OH)$_2$, etc.

Suitable reaction times are from two hours to about two days. The preparation of the physiologically acceptable salts and the esterification of the free carboxyl group with alcohols are carried out in a fully conventional manner.

Compounds of Formula I wherein $R_3$ is alkyl may also be prepared by including conventional akylation of compounds of Formula II, wherein $R_3$ is hydrogen.

If a compound of Formula II is acylated with a compound of Formula III wherein $R_6$ is hydrogen, subsequent acylation using a suitable reactive acid derivative $R_1$—CO—X, wherein X is as defined above, will produce a compound of the general Formula I.

The amines of Formula II may be prepared by fully conventional methods. For example, 5-amino-2,4,6-triiodineisophthalamic acid derivatives may be reacted with a halo-acyl halide to form 5-halogen-acylamido-2,4,6-triiodine-isophthalamic acid derivatives; and these can be converted using ammonia or an amine into a Formula III compound. When $R_4$ is lower alkyl, alkylation by known methods may be carried out on the nucleus-located amino group prior to conversion into the amine.

The new contrast media of this invention are especially suited for use in urography, angiography, bronchography, etc., for visualization of body cavities and also for computer tomography.

Compared to conventional ionic X-ray contrast media such as iothalamate, for instance, the present compounds display lower osomtic pressure. This is especially advantageous, since solutions of high concentrations are generally required in utilization of contrast media. At the same time, the compounds of this invention are characterized by high hydrophilic properties and high stability of their aqueous solutions. The combination of the pharmacology and toxicology of the compounds of this invention are also superior.

As an example of the latter superiority, comparison may be made with the compounds of U.S. Pat. Nos. 4,005,188, 4,014,986, 4,065,553, 4,065,554, 4,094,966. Such comparative data are shown in the Table below, wherein A is 5-(3-N-methylmethoxyacetamido-5-methylcarbamoyl-2,4,6-triiodine-benzamidoacetamido)-N-(2-hydroxyethyl)-2,4,6-triiodine-isophthalamic acid; B is 5-(3-N-methyl-acetamido-2,4,6-triiodine-5-methylcarbamoyl-benzamido-acetamido)-N-(2-hydroxyethyl)-2,4,6-triiodine-isophthalamic acid (Ioxaglate); and C is 5-acetamido-2,4,6-triiodine-N-methyl-isophthalamic acid. A, B and C were tested as their meglumine salts.

TABLE 1

| Compound | Tolerance LD$_{50}$ i.v. (7 days) | [mg I/kg of rat] ED$_{50}$ pericerebral (24 hours) | Protein Bond | Coefficient of Distribution |
|---|---|---|---|---|
| A | ~10,000 | ~100 | 2.5 | <0.001 |
| B | ~7,500 | ~40 | 6.8 | 0.033 |
| C | ~7,500 | 60 | 7.6 | 0.017 |

The table shows that the new compounds have a clearly improved general and neural tolerability compared to the comparison substances. It is furthermore seen from this table that the interaction of the new compounds with proteins is much less than that of the known comparison substances. The extraordinarily hydrophilic behavior of the compounds of this invention demonstrates their low distribution coefficients which were measured at a pH of 7.6 in a 1-butanol/tris-HCl buffer system.

The preparation of the new X-ray contrast media from the compounds of this invention is fully conventional. For example, the contrast compound can be combined with conventional galenic adjuvants to form a composition suitable for the desired method of application.

For example, the compounds of this invention can be employed in mixture with conventional excipients, i.e., pharmaceutically acceptable organic or inorganic carrier substances suitable for parenteral or enteral application which do not deleteriously react with the active compounds. Suitable pharmaceutically acceptable carriers include but are not limited to water, salt solutions, alcohols, vegetable oils, polyethylene glycols, gelatin, lactose, amylose, magnesium stearate, viscous paraffin, perfume oil, fatty acid monoglycerides and diglycerides, pentaerythritol fatty acid esters, hydroxy methylcellulose, polyvinyl pyrrolidone, talc, etc.

For parenteral application, particularly suitable are solutions, preferably oily or aqueous solutions, as well as suspensions or emulsions. Ampoules are convenient unit dosages.

For enteral application, particularly suitable are tablets or dragees having the talc and/or a carbohydrate carrier or binder or the like, the carrier preferably being lactose and/or corn starch and/or potato starch. A syrup or the like can be used wherein a sweetened vehicle is employed. Sustained release compositions can also be formulated wherein the active compound is protected with differentially degradable coatings, e.g., by microencapsulation, multiple coatings, etc.

The concentration of the new contrast media of this invention in aqueous media depends on the particular diagnostic method involved. The preferred concentrations and doses of the compounds of this invention, e.g., for X-ray diagnoses, are concentrations of 50–400 mg of iodine per ml and doses of 10–500 ml. Concentrations of 100–350 mg of iodine per ml are especially preferred.

The precise method and details of application depend on the organ which is to be visualized and can be determined by fully conventional considerations, e.g., in analogy with conventional media such as those mentioned above.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

5-[3-(N-methyl-methoxyacetamido)-5-methylcarbamoyl-2,4,6-triiodine-benzamido-acetamido]-N-(2-hydroxyethyl)-2,4,6-triiodine-isophthalamic acid A. Preparation of the amino starting material 5-amino-acetamido-N-(2-hydroxyethyl)-2,4,6-triiodineisophthalamic acid (a) 3-chloroacetamido-N-(2-chloroacetoxyethyl)-2,4,6-triiodine-isophthalamic acid 59.7 ml of chloroacetyl chloride is dripped with stirring within 45 minutes into 180.6 g of amino-N-(2-hydroxyethyl)-2,4,6-triiodine-isophthalamic acid in 300 ml of dimethylacetamide, with ice cooling and a maximum temperature of 15° C. The mixture is stirred overnight. Thereupon, 50 ml of water is added and stirring is continued for 30 minutes, followed by vacuum concentration, the remaining syrup being stirred with 3 liters of water overnight. The preparation is evacuated, comminuted and, following a treatment of several hours with 1.5 liters of water in vacuum at 60° C., dried for 16 hours.

Yield: 190.2 g (84%), melting point 239°–241° C.

Analysis: $C_{14}H_{11}Cl_2I_3N_2O_6$ (754.9). Computed: Cl 9.39; I 50.44. Measured: Cl 9.32; I 50.79.

(b) 94.4 g of the above bis-chloroacetyl compound is treated with 625 ml of water and 1 liter of concentrated ammonia solution for 5 days at room temperature. This is followed by concentration in vacuum, multiple afterdistillation with water, overnight stirring in 875 ml of water, evacuation of precipitate, washing until salts are removed and drying in vacuum at 60° C.

Yield: 66.9 g (81%), melting point 255°–257° C. (with decomposition).

Analysis: $C_{12}H_{12}I_3N_3O_5$ (659.0). Computed: C 21.87; H 1.83; I 57.78; N 6.38. Measured: C 21.92; H 2.08; I 57.75; N 6.37.

B. Preparing the acid chloride starting component 2,4,6-triiodine-3-(N-methyl-methoxyacetamido)-5-methylcarbamoyl-benzoic acid chloride (a) 2,4,6-triiodine-3-(N-methyl-methoxyacetamido)-5-methyl-carbamoyl-benzoic acid 36.9 ml of dimethyl sulfate is dripped into 193.2 g of 2,4,6-triiodine-3-methoxyacetamido-5-methylcarbamoyl-benzoic acid in 138 ml of 5 N soda lye with strong stirring and at a maximum temperature of 30° C. Stirring is continued overnight. The mixture then is acidified with 2 N hydrochloric acid. The precipitate is removed by evacuation, is treated for half an hour with 600 ml of water in a steam bath, then is evacuated again, washed until salt free with water and dried in vacuum at 20° C.

Crude yield: 173.5 g.

The crude product is dissolved in 660 ml of ethyl alcohol while stirring 36.4 ml of 40% methylamine solution. It is stirred for two days at room temperature and the precipitate is evacuated, post-washed with ethyl alcohol and dried in vacuum at 60° C. The salt is thereafter dissolved in 400 ml of water, treated with activated carbon, acidified with hydrochloric acid, and the free acid, following stirring, is evacuated overnight, washed until salt free with water and dried in vacuum at 70° C.

Yield: 128.3 g (65%) of pure product with a melting point of 272°–275° C. (with decomposition).

Analysis: $C_{13}H_{13}I_3N_2O_5$ (658.0). Computed: C 23.73; H 1.99; I 57.86; N 4.26; MW 658. Measured: C 23.79; H 2.12; I 57.79; N 4.21; MW 668.

(b) 98.7 g of the above acid is stirred into 450 ml of thionyl chloride while adding 3 ml of dimethylformamide for 4 hours at 65° C., the mixture being stirred overnight. It is treated with 2.25 liters of absolute ether, evacuated, post-washed with ether, and dried in vacuum at 50° C. Then the product is incorporated into 1.1 liters of chloroform, and shaken out with 200 ml of saturated sodium bicarbonate solution and three times with water. The organic phase is dried with sodium sulfate, the solvent is removed at lowered pressure and the residue is dried in vacuum at 50° C.

Yield: 94.4 g (93%), melting point: ~301° C. (with decomposition).

Analysis: $C_{13}H_{12}ClI_3N_2O_4$ (676.4). Computed: C 23.08; H 1.79; N 4.14. Measured: C 22.87; H 1.88; N 4.09.

(c) 54.1 g of 2,4,6-triiodine-3-(N-methyl-methoxyacetamido)-5-methylcarbamoyl-benzoic acid chloride is added to a suspension of 55.4 g of 5-aminoacetamido-N-(2-hydroxyethyl)-2,4,6-triiodine-isophthalamic acid in 80 ml of dimethyl acetamide with addition of 25.5 ml of triethylamine. The mixture is stirred for three hours at 50° C. and then overnight at room temperature. Where appropriate, it is filtered free from some small undissolved components. It is then diluted with 1 liter of water. The slightly cloudy solution is treated with activated carbon and the carbon is then removed. The solution is acidified with 50 ml of concentrated hydrochloric acid. Thereupon stirring proceeds overnight, the precipitate is removed, the mixture is washed with some water and dried in vacuum at 60° C. After the dry preparation is stirred with 700 ml of water for 16 hours, it is evacuated, washed until salt free and dried in vacuum at 60° C.

Yield: 68.8 g (66%), melting point 292° C. (with decomposition).

Analysis: $C_{25}H_{23}I_6N_5O_9$ (1298.9) Computed: C 23.12; H 1.78; I 58.62; MW 1299. Measured: C 23.11; H 1.77; I 58.53; MW 1289.

EXAMPLE 2

5-[3-(N-methyl-acetamido)-5-methylcarbamoyl-2,4,6-triiodine-benzamido-acetamido]-N-(2-hydroxy-1-methylcarbamoylethyl)-2,4,6-triiodine-isophthalamic acid Preparing the amino starting component

A.
5-aminoacetamido-N-(2-hydroxy-1-methylcarbamoylethyl)-2,4,6-triiodine-isophthalamic acid (a) 35.8 ml of chloroacetyl chloride is dripped into 98.9 g of 5-amino-N-(2-hydroxy-1-methylcarbamoylethyl)2,4,6-triiodine-isophthalamic acid in 150 ml of dimethyl formamide with ice cooling and stirring within 40 minutes at a maximum temperature of 15° C., the mixture then being stirred in the ice bath for one hour and subsequently at room temperature overnight. The solution is then dripped into 2 liters of water with stirring, and stirred further for 16 hours. The precipitate is removed, treated with water for a few hours, evacuated, washed with water until salt free, and dried in vacuum.

(b) The 103.5 g (85%) of bis-N,O-chloroacetyl compound so obtained has a melting point of 190°–193° C. and is left to stand in 1020 ml of concentrated ammonia with addition of 640 ml of water for 8 days while excluding light, concentrated in vacuum and post-distilled several times with water. The residue is heated for one hour in the steam bath in 500 ml of water and stirred overnight at room temperature. The preparation is evacuated, post-washed with water and dried in vacuum at 60° C.

Yield: 45.6 g (50%), melting point 255°–257° C. (with decomposition).

Analysis: $C_{14}H_{15}I_3N_4O_6$ (716.0) Computed: C 24.48; H 2.11; I 53.17; N 7.83; MW 716. Measured: C 23.49; H 2.08; I 53.14; N 7.85; MW 720.

B. 32.3 g of 2,4,6-triiodine-3-(N-methylacetamido)-5-methylcarbamoyl-benzoic acid chloride and 15.9 ml of triethylamine are added to 35.8 g of the above amino compound in 50 ml of dimethylacetamide, the mixture then being stirred for 3 hours at 50° C. and overnight at room temperature. The reaction solution then is incorporated into 650 ml of water and treated for one hour with 10 g of activated carbon. After removing the carbon, the filtrate is acidified with 50 ml of concentrated hydrochloric acid and stirred overnight at room temperature. Thereupon the precipitate is evacuated, and the dry product is mixed with fresh water, evacuated, washed with water and dried in vacuum at 60° C.

Yield: 33.7 g (51%), melting point: ~276° C. (with decomposition).

Analysis: $C_{26}H_{24}I_6N_6O_9$ (1325.9). Computed: C 23.55; H 1.82; I 57.43; N 6.34; MW 1326. Measured: C 23.65; H 1.84; I 57.70; N 6.29; MW 1332.

EXAMPLE 3

5-[3-(N-methyl-acetamido)-5-methylcarbamoyl-2,4,6-triiodine-benzamido-acetamido]-2,4,6-triiodine-N-(methylcarbamoylmethyl)-isophthalamic acid.

A. Preparing the initial component 5-aminoacetamido-2,4,6-triiodine-N-methylcarbamoylmethyl-isophthalamic acid (a)
3-chloroacetamido-2,4,6-triiodine-N-methylcarbamoylmethyl-isophthalamic acid The preparation is analogous to that of Example 1A (a), from 78.6 g of 3-amino-2,4,6-triiodine-N-methylcarbamoylmethyl-isophthalamic acid and 29.8 ml of chloroacetyl chloride.

Yield: 79.5 g (90%), melting point 290°–291° C. (with decomposition).

Analysis: $C_{13}H_{11}ClI_3N_3O_5$ (705.4). Computed: C 22.13; H 1.57; Cl 5.03; I 53.97; N 5.96. Measured: C 22.19; H 1.50; Cl 5.32; I 53.48; N 5.97.

(b) By treating 70.5 g of the above chloroacetyl preparation with 800 ml of concentrated ammonia, while adding 500 ml of water for a duration of 8 days, the amino compound corresponding to that of Example 1A (b) is obtained.

Yield: 55.9 g (82%), melting point 258°–259° C. (with decomposition).

Analysis: $C_{13}H_{13}I_3N_4O_5$ (686, O). Computed: C 22.76; H 1.91; I 55.50; N 8.17. Measured: C 22.50; H 2.13; I 55.60; N 8.20.

(c) Analogously to Example 2B, the title compound is prepared from the above amino compound and 2,4,6-triiodine-3-(N-methyl-acetamido)-5-methylcarbamoyl-benzoic acid chloride in dimethylacetamide.

Melting point: 272° C. (with decomposition).

Analysis: $C_{25}H_{22}I_6N_6O_8$ (1295,9). Computed: C 23.17; H 1.71; I 58.76; N 6.49; MW 1296. Measured: C 23.22; H 1.66; I 58.40; N 6.39; MW 1288.

EXAMPLE 4

5-(3-acetamido-5-methylcarbamoyl-2,4,6-triiodinebenzamido-acetamido)-N-(2-hydroxy-1-methylcarbamoylethyl)-2,4,6-triiodine-isophthalamic acid

A.
5-(3-amino-5-methylcarbamoyl-(2,4,6-triiodinebenzamido-acetamido)-N-(2-hydroxy-1-methylcarbamoylethyl)-2,4,6-triiodine-isophthalamic acid 29.5 g of 3-amino-2,4,6-triiodine-5-methylcarbamoylbenzoic acid chloride is added to 35.8 g of 5-aminoacetamido-N-(2-hydroxy-1-methylcarbamoylethyl)-2,4,6-triiodine-isophthalamic acid (Example 2A) in 50 ml of dimethylacetamide and 15.9 ml of triethylamine and stirred for 3 hours at 50° C. and thereafter at room temperature. Then 650 ml of water are added, the solution is treated with activated carbon, and after removing the carbon, the solution is acidified with 50 ml of concentrated hydrochloric acid. The precipitate is evacuated, stirred with 500 ml of water and, following renewed evacuation and washing with water, is dried in vacuum at 60° C.

Yield: 32.6 g (51%), melting point 253°–255° C. (with decomposition).

Analysis: $C_{23}H_{20}I_6N_6O_8$ (1269.9). Computed: C 21.75; H 1.59; I 59.96; N 6.62; MW 1270. Measured: C 21.91; H 1.68; I 60.29; N 6.65; MW 1260.

B. 3.6 ml of acetyl chloride is dripped into 19.0 g of the above amino compound in 36 ml of dimethylacetamide at 0° C. with stirring. It is stirred overnight at room temperature and, following addition of some water, stirred for another 30 minutes. Following concentration in vacuum, the residue is stirred into 200 ml of water, the precipitate is evacuated and then dissolved in 50 ml of 2 N soda lye and 150 ml of water. The solution is treated with activated carbon and after removing the carbon, the filtrate is acidified with 20 ml of concentrated hydrochloric acid and stirred overnight at room temperature. Then the preparation is isolated, heated to boiling in 100 ml of water, evacuated following cooling, washed until salt free and dried in vacuum at 70° C.

Yield: 12.4 g (63%), melting point ~263° C. (with decomposition).

Analysis: $C_{25}H_{22}I_6N_6O_9$ (1311.9). Computed: C 22.89; H 1.69; I 58.04; N 6.41. Measured: C 22.90; H 1.70; I 57.74; N 6.27.

EXAMPLE 5

5-[3-(N-methyl-acetamido)-5-methylcarbamoyl-2,4,6-triiodine-N-methylbenzamido-acetamido]-N-(2-hydroxyethyl)-2,4,6-triiodine-isophthalamic acid

A. Preparing the amino starting component 5-methylaminoacetamido-N-(2-hydroxyethyl)-2,4,6-triiodine-isophthalamic acid The preparation is similar to that for the amino compound of Example 1A from 56.6 g of 3-chloroacetamido-N-(2-chloroacetoxyethyl)-2,4,6-triiodine-isophthalamic acid (Example 1A.a)) and 600 ml of 40% aqueous methylamine with addition of 375 ml of water.

Yield: 42.6 g (84%), melting point 247°–249° C. (with decomposition).

Analysis: $C_{13}H_{14}I_3N_3O_5$ (673.0). Computed: C 23.20; H 2.10; I 56.57; N 6.24; MW 673. Measured: C 23.28; H 2.10; I 56.62; N 6.13; MW 674.

B. Preparing the title compound

By reacting 33.7 g of the above compound with 32.3 g of 2,4,6-triiodine-3-(N-methyl-acetamido)-5-methylcarbamoylbenzoic acid chloride in 100 ml of dimethylformamide, the title compound as described in Example 2, is obtained.

Yield: 46 g (72%), melting point about 310° C. (with decomposition).

Analysis: $C_{25}H_{23}I_6N_5O_8$ (1282.9). Computed: C 23.40; H 1.81; I 59.35; N 5.46; MW 1283. Measured: C 23.72; H 1.97; I 59.10; N 5.60; MW 1289.

EXAMPLE 6

Preparing a ready-to-use methyl glucamine salt solution

| | |
|---|---|
| 5-[3-(N-methyl-methoxyacetamido)-5-methylcarbamoyl-2,4,6-triiodine-benzamido-acetamido]-N-(2-hydroxyethyl)-2,4,6-triiodine-isophthalamic acid | 648.2 g |
| N-methylglucamine | 97.3 g |
| calcium disodium edetate | 0.1 g |
| bidistilled water filled to | 1000.0 ml |

The solution is filled into ampoules or multivials and sterilized at 120° C. It contains 380 mg of iodine per ml.

EXAMPLE 7

Preparing a ready-to-use methyl glucamine salt solution

| | |
|---|---|
| 5-[3-(N-methyl-acetamido)-5-methylcarbamoyl-2,4,6-triiodine-benzamidoacetamido]-N-(2-hydroxy-1-methylcarbamoyl-ethyl)-2,4,6-triiodine-isophthalamic acid | 522.4 g |
| n-methyl glucamine | 76.8 g |
| calcium disodium edetate | 0.1 g |
| bidistilled water filled to | 1000.0 ml |

The solution is filled into ampoules or multivials and sterilized at 120° C. It contains 300 mg of iodine per ml.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of the formula

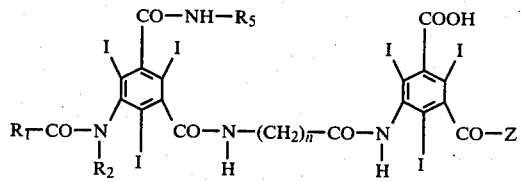

wherein $R_1$ is $C_{1-4}$ alkyl, $C_{1-4}$ alkyl substituted by OH or $C_{1-2}$ alkoxy; $R_2$ is hydrogen or $C_{1-4}$ alkyl; Z is —A—$NHCH_3$ or when $R_1$ is alkyl substituted by OH or alkoxy, Z can also be hydroxy $C_{2-5}$ alkylamino; $R_5$ is $C_{1-4}$ alkyl or $C_{1-4}$ alkyl substituted by OH; n is 1, 2 or 3; and A is

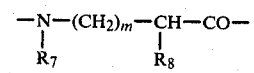

wherein $R_7$ is H or $C_{1-4}$ alkyl; $R_8$ is H, $C_{1-4}$ alkyl or $C_{1-4}$ alkyl substituted by OH or $C_{1-2}$ alkoxy; or together $R_7$ and $R_8$ form a propylene or hydroxypropylene ring; and m is 0 or 1;

or an ester thereof with a $C_1$–$C_4$ alkanol or a physiologically acceptable salt thereof with a base.

2. A compound of claim 1, wherein $R_1$ has 1–2 carbon atoms, $R_5$ has 1–2 carbon atoms and n is 1.

3. 5-[3-(N-methyl-methoxyacetamido)-5-methylcarbamoyl-2,4,6-triiodine-benzamido-acetamido]-N-(2-hydroxyethyl)-2,4,6-triiodine-isophthalamic acid, a compound of claim 1.

4. 5-[3-(N-methyl-acetamido)-5-methylcarbamoyl-2,4,6-triiodine-benzamido-acetamido]-N-(2-hydroxy-1-methylcarbamoylethyl)-2,4,6-triiodine-isophthalamic acid, a compound of claim 1.

5. 5-[3-(N-methyl-acetamido)-5-methylcarbamoyl-2,4,6-benzamido-acetamido]-2,4,6-triodine-N-(methylcarbamoylmethyl)isophthalamic acid, a compound of claim 1.

6. 5-(3-acetamido-5-methylcarbamoyl-2,4,6-triiodinebenzamido-acetamido)-N-(2-hydroxy-1-methylcarbamoylethyl)-2,4,6-triiodine-isophthalamic acid, a compound of claim 1.

7. An X-ray contrast medium, comprising an amount of a compound of claim 1 effective as a contrast medium and a pharmaceutically acceptable carrier.

8. A method of visualizing an internal organ of a patient which comprises administering to the patient an amount of a compound of claim 1 effective as an X-ray contrast medium and exposing the organ to X-ray diagnostic treatment.

9. A compound of claim 1 wherein $R_5$ is $C_{1-4}$ alkyl; $R_7$ is H; and $R_8$ is H or $C_{1-4}$ alkyl substituted by OH.

10. A compound of claim 9 wherein n is 1.

11. A compound of claim 1 wherein Z is —A—NHCH$_3$.

12. A compound of claim 1 wherein Z is hydroxy$C_{2-5}$alkylamino and $R_1$ is $C_{1-4}$alkyl substituted by $C_{1-2}$alkoxy.

13. A compound of claim 1 wherein Z is hydroxy$C_{2-5}$alkylamino and $R_1$ is monohydroxy substituted alkyl.

* * * * *